United States Patent
Birkenbach et al.

(10) Patent No.: US 9,030,444 B2
(45) Date of Patent: May 12, 2015

(54) CONTROLLING AND/OR OPERATING A MEDICAL DEVICE BY MEANS OF A LIGHT POINTER

(75) Inventors: Rainer Birkenbach, Erding (DE); Alexander Urban, Forstinning (DE); Alexander Druse, Munich (DE); Elmar Schlereth, Munich (DE)

(73) Assignee: Brainlab AG, Feldkirchen (DE)

( * ) Notice: Subject to any disclaimer, the term of this patent is extended or adjusted under 35 U.S.C. 154(b) by 185 days.

(21) Appl. No.: 13/511,412

(22) PCT Filed: Jan. 14, 2010

(86) PCT No.: PCT/EP2010/050406
§ 371 (c)(1),
(2), (4) Date: May 23, 2012

(87) PCT Pub. No.: WO2011/085814
PCT Pub. Date: Jul. 21, 2011

(65) Prior Publication Data
US 2012/0235909 A1 Sep. 20, 2012

(51) Int. Cl.
G06F 3/042 (2006.01)
G06F 3/038 (2013.01)
G06F 3/0354 (2013.01)
A61B 17/00 (2006.01)
A61B 19/00 (2006.01)

(52) U.S. Cl.
CPC ..... G06F 3/0386 (2013.01); A61B 2017/00207 (2013.01); A61B 2019/2269 (2013.01); A61B 2019/5229 (2013.01); A61B 2019/5231 (2013.01); G06F 3/03542 (2013.01)

(58) Field of Classification Search
CPC . G06F 3/0308; G06F 3/0325; G06F 3/03542; G06F 3/0386; G06F 3/0317; G06F 3/0321; G06F 3/0425

USPC .............. 345/156–186; 353/42; 348/135, 141
See application file for complete search history.

(56) References Cited

U.S. PATENT DOCUMENTS 4,898,555 A * 2/1990 Sampson ........................ 445/22
5,911,036 A 6/1999 Wright et al.
(Continued)

FOREIGN PATENT DOCUMENTS

DE 20 2009 012624 U1 11/2009
WO 2008/104082 A1 9/2008

OTHER PUBLICATIONS

International Search Report for International Application No. PCT/EP2010/050406 dated Oct. 4, 2010.

*Primary Examiner* — Liliana Cerullo
(74) *Attorney, Agent, or Firm* — Tucker Ellis LLP

(57) ABSTRACT

The invention relates to a system for controlling and/or operating a medical device (30) associated with a display (20; 50) on which medical images (24) and/or control and/or operating elements (21, 22, 25) are displayed, wherein the system comprises: —a light pointer (10; 40) which projects a delimited light cursor (14; 44); —a light detection device which is associated with the display and comprises a sensor (23) for determining the presence and location of the light cursor (14; 44) projected by the light pointer (10; 40); and—a converter (26) which converts the captured presence and location information into control and/or operating commands for the medical device. The invention also relates to a method for controlling and/or operating a medical device (30) associated with a display (20; 50) on which medical images (24) and/or control and/or operating elements (21, 22, 25) are displayed, wherein a delimited light cursor (14; 44) is projected onto the display (20; 50) by means of a light pointer (10; 40), wherein the presence and location on the display (20; 50) of the light cursor (14; 44) projected by the light pointer (10; 40) is detected by means of a sensor (23), and wherein the captured presence and location information is converted into control and/or operating commands for the medical device (30).

9 Claims, 4 Drawing Sheets

(56) References Cited

U.S. PATENT DOCUMENTS

| | | | |
|---|---|---|---|
| 7,009,663 B2* | 3/2006 | Abileah et al. | 349/12 |
| 2007/0273838 A1 | 11/2007 | Hong et al. | |
| 2008/0097176 A1* | 4/2008 | Music et al. | 600/323 |
| 2009/0046146 A1 | 2/2009 | Hoyt | |
| 2009/0167728 A1* | 7/2009 | Geaghan et al. | 345/179 |
| 2010/0036393 A1* | 2/2010 | Unsworth | 606/130 |

* cited by examiner

CONTROLLING AND/OR OPERATING A MEDICAL DEVICE BY MEANS OF A LIGHT POINTER

This application is a national phase of International Application No. PCT/EP2010/050406 filed Jan. 14, 2010 and published in the English language.

The present invention relates to controlling and/or operating a medical device by means of a light pointer. In particular, a system for controlling and/or operating a medical device and a method for the same purpose are provided. Operating and/or controlling medical devices, for example in an operating theater, is often cumbersome or problematic for physicians in terms of maintaining high levels of sterility. Medical devices used in operating theaters such as surgical or medical navigation systems, for which the present invention is particularly suitable, have in the past been operated and/or controlled in various ways, which each have their own problems.

Known control and/or operation systems employ several different modes of interaction between a user and a navigation system, including for example touch screens, keyboards and mouses, voice control or remote control. If touch screens are used (in most cases, the screens used as the navigation system display), it is necessary to maintain their sterility by draping them with sterile drapes or by using a sterile touching device such as a sterile pen. Sterile drapes placed over a screen impair the image quality, in particular when the screen is touched with contaminated hands. Moreover, touching a draped screen with gloved hands can lead to imprecise inputs owing to poor sensual feedback. Using a sterile pen in conjunction with a display with no drapes allows for good image quality, but still incurs a number of general problems. One of these problems is that a user still needs to approach the display in order to interact with the navigation system and may thus be forced to leave their working position. Moreover, such pens are expensive and there is still some risk to sterility, for example if a sterile pen touches an unsterile display or monitor. To avoid such a risk, pens often have to be exchanged a number of times during an operation.

The use of keyboards and mouses is rather cumbersome and not intuitive, and there are always problems in providing special keyboards and mouses which can be kept sterile.

The use of voice control is not generally accepted, on the one hand because of the necessity to wear a microphone and on the other hand because of technical problems in identifying spoken commands. Remote controls can be used in sterile bags, but do not generally allow for intuitive control.

As briefly discussed above, the present invention is particularly useful and applicable in connection with surgical or medical navigation systems, one of which is for example known in general terms from DE 196 39 615 A1, which are employed in assisting medical personnel in planning and carrying out medical procedures. Such navigation systems can for example be used in conjunction with instrument tracking systems in order to show, on a display, a positional relationship between instruments and a patient's body or parts of a patient's body, images of which have been acquired beforehand, for example as CT or MR image data sets. The navigation system can also be used to guide a user through a sequence of steps to be carried out during a medical procedure.

An input apparatus for a computer system using a pointer device is proposed, for different purposes, in U.S. Pat. No. 7,547,025 B2.

It is the object of the present invention to provide a system and method for controlling and/or operating a medical device which overcome the aforementioned problems of the controlling and/or operating systems and methods according to the prior art. In particular, an easy-to-manage way of controlling and/or operating medical devices is to be proposed which in particular avoids interruptions to the workflow and/or sterility problems.

A medical device as used in conjunction with the present invention can be referred to in general terms as an operation-assisting medical device or a medical device used in an operating theater. Although the present invention is mainly explained herein with respect to a medical navigation system, it is not limited to such an application or such a medical device. Other medical devices, in particular those used in an operating theater, can also be controlled and/or operated by employing the present invention, such as for example any device which can be turned on or off or switched to another mode of operation, such as lamps, movable couches, fluoroscopic devices, etc.

The present invention is defined by claim 1 which relates to a control and/or operating system for a medical device and by claim 12 which relates to a method for controlling and/or operating a medical device. The sub-claims define advantageous embodiments of the present invention.

The system according to the present invention controls and/or operates a medical device associated with a display on which medical images and/or control elements and/or operating elements are displayed. The system comprises: a light pointer which projects a delimited light cursor; a light detection device which is associated with the display and comprises a sensor for determining the presence and location of the light cursor projected by the light pointer; and a converter which converts the captured presence and location information into control and/or operating commands for the medical device.

In other words, the system of the invention comprises a light pointer, the pointing spot of which can be detected by a sensitive display, such that the medical device is controlled and/or operated, i.e. such that for example a virtual button is "pushed" or a certain area on the display is marked and/or highlighted. Thus, the present invention controls a medical device by means of remote control, using a light spot which offers a variety of advantages, especially in the field of application for which the present invention is primarily intended. One of the main advantages is that an easy-to-manage remote control system is provided, wherein the controlling and/or operating action can be carried out at the working location of the user—for example, a surgeon. The user does not have to leave the place they are currently working at, in order to approach the display, but can instead "transmit" a "light command". This enables a fluent working sequence. The sterility of the user is not affected by controlling and/or operating the device because no potentially unsterile input device has to be touched.

In accordance with one embodiment, the light pointer comprises a switch, a multi-deck switch or a number of switches for controlling its light projection. Additionally or alternatively, the laser pointer can comprise switchable or selectable light sources of one or more wavelengths, or a wavelength modifier, as its light source. Additionally or alternatively, the laser pointer can also comprise a switchable or controllable cursor-forming unit for forming the projected light cursor, in particular a light slit or a lens or an object lens. All of the above features can help to produce and/or modify the light signal emitted by a light pointer, in order to create a variety of different control or operating commands or inputs. These individual commands can of course also complement each other in order to achieve an optimum mode of control for the medical device.

In a preferred embodiment of the present invention, the light pointer is a laser pointer which produces a finely delimited or formable cursor. Other light pointers can of course also be used, providing they are able to deliver a well-defined and sufficiently bright light spot.

The light detection device can comprise a photosensitive surface or layer on the display, in particular on a monitor screen, in particular a touch screen. In technical terms, location detection as employed using touch screens or multi-touch screens can be used to set up such displays, while the presence of a light cursor can be detected by photosensitive elements which are integrated into said system and determine the location of the cursor on the display. The screen can of course additionally exhibit touch screen properties, such that a combination of light cursor inputs and touch inputs can be made and used.

The light detection device can be set up in such a way that it comprises a position-detecting light grid or laser grid covering the surface of the display which is, in a preferred embodiment, a monitor screen. Alternatively or additionally, the light detection device can comprise a camera or a camera system which monitors the display.

In accordance with one embodiment of the system of the invention, the display is a projection screen and the system also comprises an image projector which projects the medical images and/or the control elements and/or operating elements of the medical device onto the projection screen. This is particularly useful if rather large displays are needed, for example if an ongoing treatment and its image assistance is to be shown to a larger number of people, for example during a demonstration or presentation.

The display surface can be a light-reflecting surface or can be covered with a light-reflecting layer which preferably reflects light at the wavelength emitted by the light pointer. It may also be advantageous to choose a reflecting surface which solely or mainly reflects said wavelength, in order to avoid image interference. The surface of a monitor can of course be subjected to a corresponding treatment in order to acquire said reflection properties.

In accordance with one aspect of the invention, the medical device is a medical or surgical navigation or treatment planning system. When using such a surgical or medical navigation system or treatment planning system, there is a need for interaction between the user and the navigation system, for example in order to effect control inputs. This can include various kinds of control inputs, for example control inputs for activating a certain procedure or for advancing one step in a sequence of navigationally assisted steps in a procedure. Other control and/or operating functions can also be carried out in accordance with the present invention, such as for example marking and/or highlighting a certain portion of a medical image for registration purposes.

The invention also relates to a method for controlling a medical device associated with a display on which medical images and/or control and/or operating elements are displayed, wherein a delimited light cursor is projected onto the display by means of a light pointer, wherein the presence and location on the display of the light cursor projected by the light pointer is detected by means of a sensor, and wherein the captured presence and location information is converted into control and/or operating commands for the medical device.

The method in accordance with the invention can of course also be used to control and/or operate a medical device in accordance with the examples given above, i.e. by using the systems described or parts of these systems.

Various other aspects of the method in accordance with the present invention involve controlling and/or operating the medical device in one or more of the following ways:

a control command or input is effected by pointing the light cursor at a spot for a predetermined and/or extended period of time;

a control command or input is effected by pointing the light cursor at a spot, projecting the cursor at a first wavelength in order to highlight an element on the display and then changing the wavelength in order to effect a control and/or operating command with respect to the element;

a control command or input is effected by pointing the light cursor at a spot and then projecting a predetermined succession of light beams in order to effect a control and/or operating command with respect to the element;

a control command or input is effected by pointing the light cursor at a spot in order to highlight an element on the display and then projecting a predetermined succession of light beams in order to effect a control and/or operating command with respect to the element;

a control command or input is effected by pointing the light cursor at a spot on the display and then projecting a predetermined succession of light beams in order to effect a control and/or operating command with respect to the element;

a control command or input is effected by pointing the light cursor at a spot on the display in order to highlight an element on the display and then projecting a predetermined succession of light beams in order to effect a control and/or operating command with respect to the element;

a control command or input is effected by pointing the light cursor at a spot on the display and then altering the form of the cursor in order to effect a control and/or operating command with respect to the element;

a control command or input is effected by pointing the light cursor at a spot on the display in order to highlight an element on the display and then altering the form of the cursor in order to effect a control and/or operating command with respect to the element;

the cursor is made visible by highlighting an element on the display by means of a control software for the display.

Other embodiments of the present invention may involve using one or more cameras of the navigation or tracking system to track the light point or laser cursor. The light pointer can be integrated into any instrument or can also be a separate light pointer. It can be attached to an instrument or any other item used in the medical environment by a clip or other fastening means. It can also be integrated into gloves (surgical gloves), into glasses which are sometimes used by surgeons or into a head band. The light pointer can be embodied as a single-use, sterile/disposable light pointer. Another embodiment of the light pointer is provided in a sterile bag which the projected light beam can penetrate.

In its integrated version, the light pointer can be integrated with a variety of items, for example hardware pointers, other hand-held instruments or hand-held parts of navigation systems. One highly integrated version would be to use a laser light projector which in its original function is used as a registration aid for surface-matching registration purposes. While it has been discussed above that the display can be reflective, another way of making the location of the cursor visible is also contemplated by the present invention, wherein the light detection device determines whether the cursor is hitting the display and the graphical software itself highlights this point on the display, such that reflection is not necessary.

The invention will now be explained in greater detail by referring to specific embodiments. It should be noted that each of the features of the present invention as referred to herein can be implemented separately or in any expedient combination. In the attached drawings.

Figure 1:
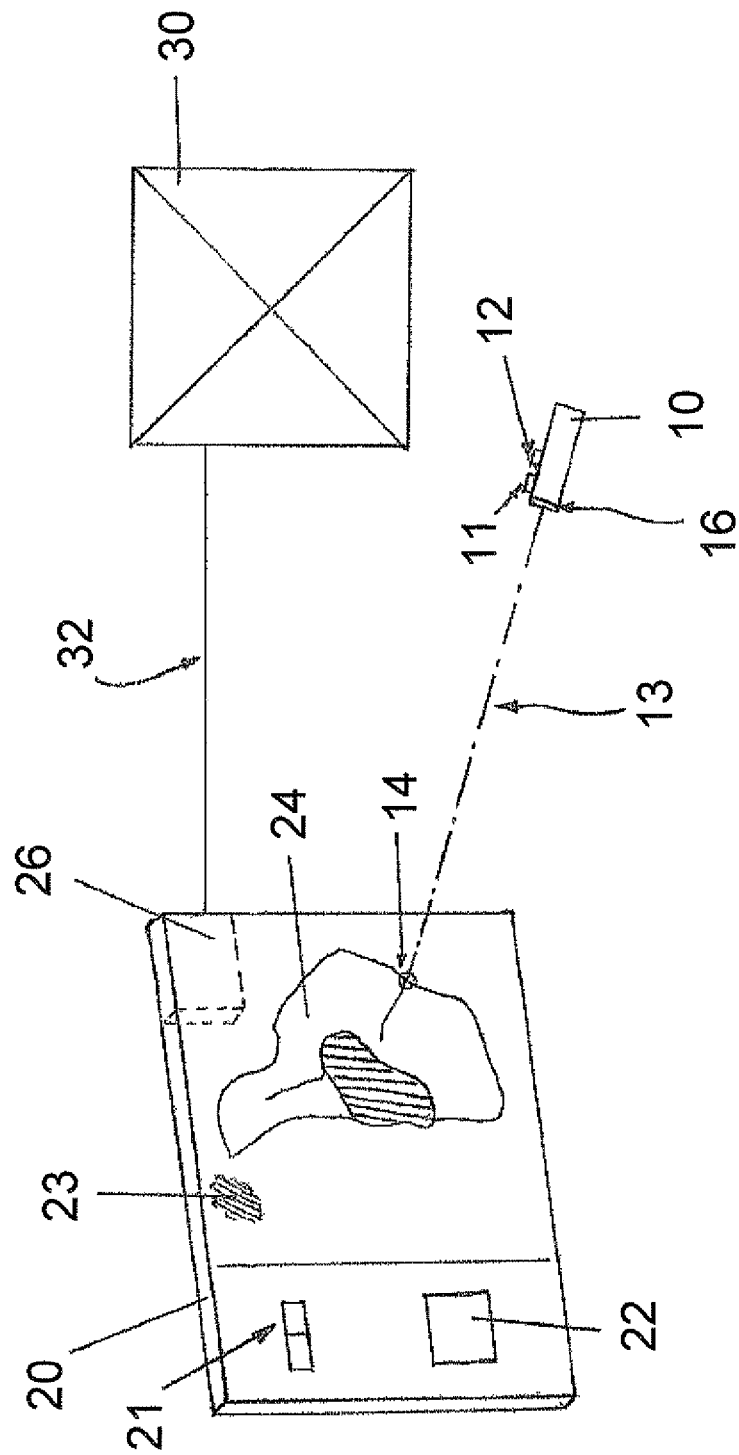
FIG. 1 depicts a first embodiment of a system in accordance with the invention, used to highlight a part of a medical image.

A first embodiment of a system in accordance with the present invention is shown in FIG. 1. A light pointer, embodied in this case by a laser pointer 10, is used to project a light beam 13 onto the display 20 of a medical navigation system 30. The laser pointer 10 has two buttons 11 and 12 which can be used to influence the properties of the projected light beam 13, for example to change its color or wavelength in order to transfer different information/commands for different control and/or operation purposes. The laser pointer 10 in FIG. 1 can also to seen to comprise, on its front end, a beam-shaping unit 16 which can consist of a variable light gap or a lens or an object lens which can alter the form and/or intensity of the beam 13, again for the purpose of effecting various different control and/or operating functions. The unit 16 for shaping the beam or changing its intensity or color can be used in conjunction with the above-mentioned functions of the buttons 11 and 12, or the buttons 11 and 12 and the unit 16 can be used separately.

The display 20 can be a monitor on which a display is shown and controlled by the navigation system 30 which is connected to the display by a wired or wireless connection 33 for this purpose. Particular input elements or "software buttons" 21, 22 are shown on the display 20, as well as a patient image taken beforehand, which bears the reference numeral 24. Such a patient image 24 may be one of an image data set produced by a CT or MR unit.

Reference numeral 23 is intended to show how the surface of the display 20 has a certain property which is achieved by surface treatment, by selecting an appropriate surface or by applying an appropriate surface cover or covering layer. In the present case, the surface 23 is embodied to be reflective, so that the cursor 14 produced by the light beam 13 can be seen on the display 20. The user producing the cursor 14 on the display 20 will then see exactly the location which the cursor 14 is pointing at. In the present example, the cursor 14 is pointing at a particular landmark on the patient image. Said landmark is for example highlighted if the cursor lingers on it for more than three seconds, and a click on a button or a change effected at the unit 16 can then mark the cursor for a special task, for example for registering said landmark for navigation purposes. The display 20 is equipped with a light detection device which determines the presence and location of the light cursor 14, and the respective information is collected in a converter 26 which converts it into signals which are transferred to the navigation system 30 via the connection 32, i.e. the commands and/or inputs issued by the laser pointer 10 via its cursor 14 on the display 20 are sent to the navigation system 30 via the converter 26. The navigation system 30 can then send back a signal or control command to the display 20 in order to change the display, for example in order to prompt the surgeon to choose the next registration landmark.

Figure 2:
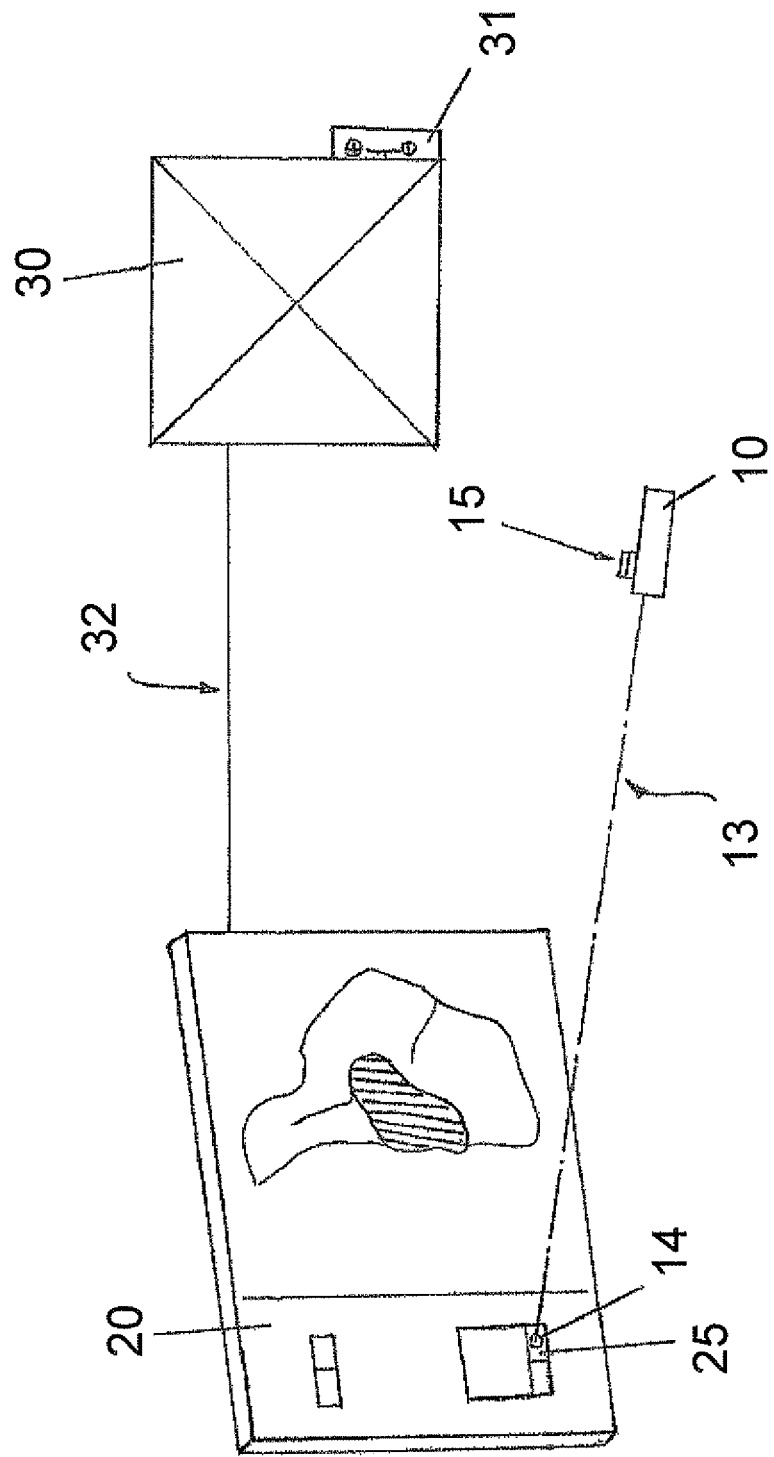
FIG. 2 depicts a second embodiment of the system in accordance with the invention, used to operate and/or control a navigation system.

Another embodiment of the present invention is shown in FIG. 2. It should be noted that elements in the figures which bear the same or similar reference numerals are either the same elements or functionally similar elements, for which reason the explanation of their functions will not be repeated here. There are three main differences between the systems of FIGS. 1 and 2. One of these differences relates to the design of the button or buttons on the laser pointer 10. The button 15 shown in FIG. 2 is a single button which is however schematically shown to have two areas. This is intended to indicate that the button is a two-deck button which exhibits a first triggering point and a second triggering point following the first triggering point, comparable to the release on a photographic camera. In the system of FIG. 2, it can be seen that a software button 25 shown on the display 20 is being pointed at with the beam 13 of the laser pointer 10 via the cursor 14. To this end, the user presses the button 15 down as far as the first triggering point, as a result of which the laser beam is produced and positions the cursor 14 on the software button 25. Once certain that the button 25 has been correctly targeted, the user can then press the button 15 down further, as far as the second triggering point, which changes the properties of the light beam 13 (for example its color, form, etc.), wherein this change sends an "activate" command to the display 20. Upon receiving this command, the software in the navigation system 30 will know that the button 25 has been activated and will accordingly carry out a particular control feature, such as for example proceeding to the next image.

Another feature shown in FIG. 2 is the supporting and charging means 31, which in the present example is attached to the navigation system 30. Said supporting and charging means 31 can be used to hold the pointer 10 while it is not in use, and to recharge its batteries.

Figure 3:
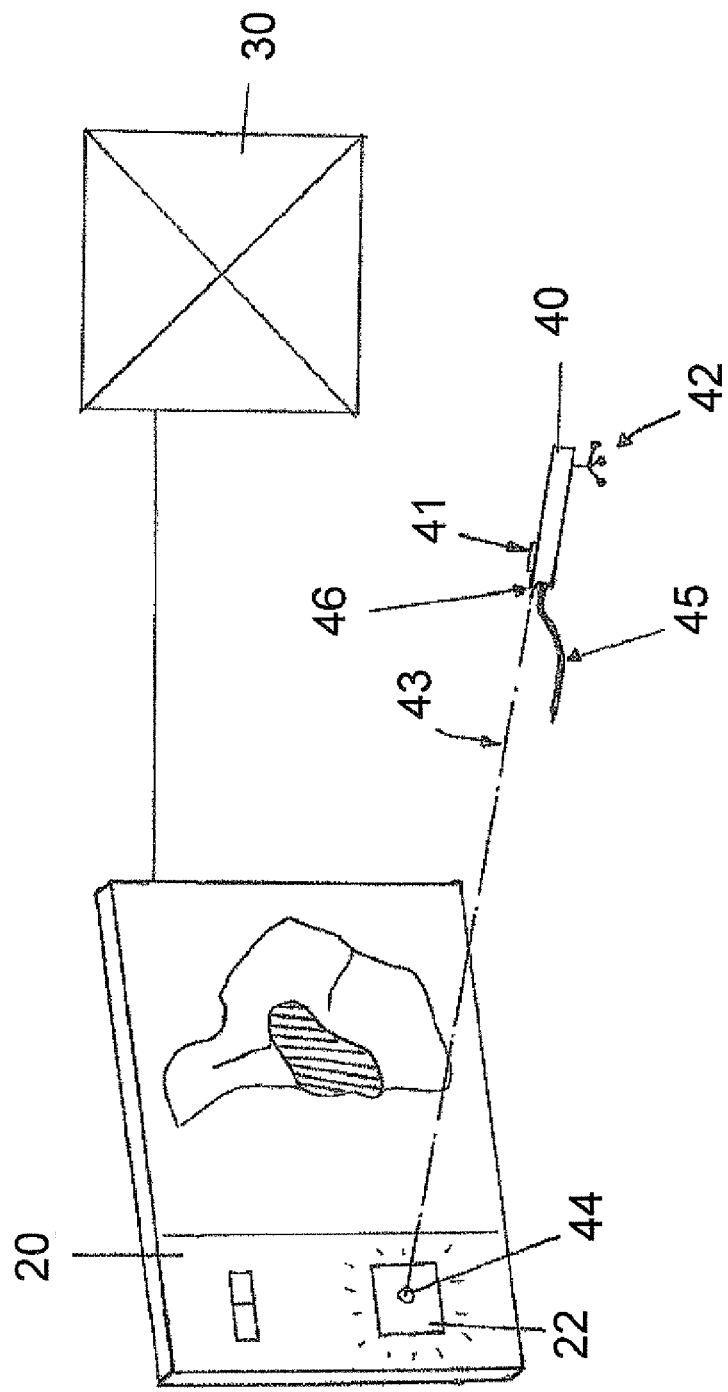
FIG. 3 depicts a third embodiment of the system in accordance with the invention, using a light pointer integrated in a hardware pointer.

FIG. 3 shows another two features which can be embodied by a system in accordance with the present invention. FIG. 3 shows that the laser pointer need not be provided as a single, separate unit but may also be provided as a laser pointer unit 46 which is permanently or removably attached to a surgical instrument, said instrument (in this case) being a hardware pointer 40 comprising a pointer tip 45 and a navigation or tracking reference 42. The pointer 40 is again equipped with a button 41 for activating a light beam 43 in order to produce a cursor 44. In the present example, the cursor 44 is positioned on a target button (software button) 22 on the display 20. The user presses down on the button 41 in order to produce a steady beam 43 onto said software button 22, for example for three seconds. This is detected by the software employed in the display/navigation system 30, and the button 22 is then highlighted by the software in order to indicate to the user that said button is now targeted and ready to be "pressed". A "pressing" signal could be produced by the user, also using a single button, for example by briefly pressing the button twice, in the manner of a "double-click". The command issued can then again operate and/or control the entire system in a predetermined way—for example, a certain navigation procedure can be initiated.

Figure 4:
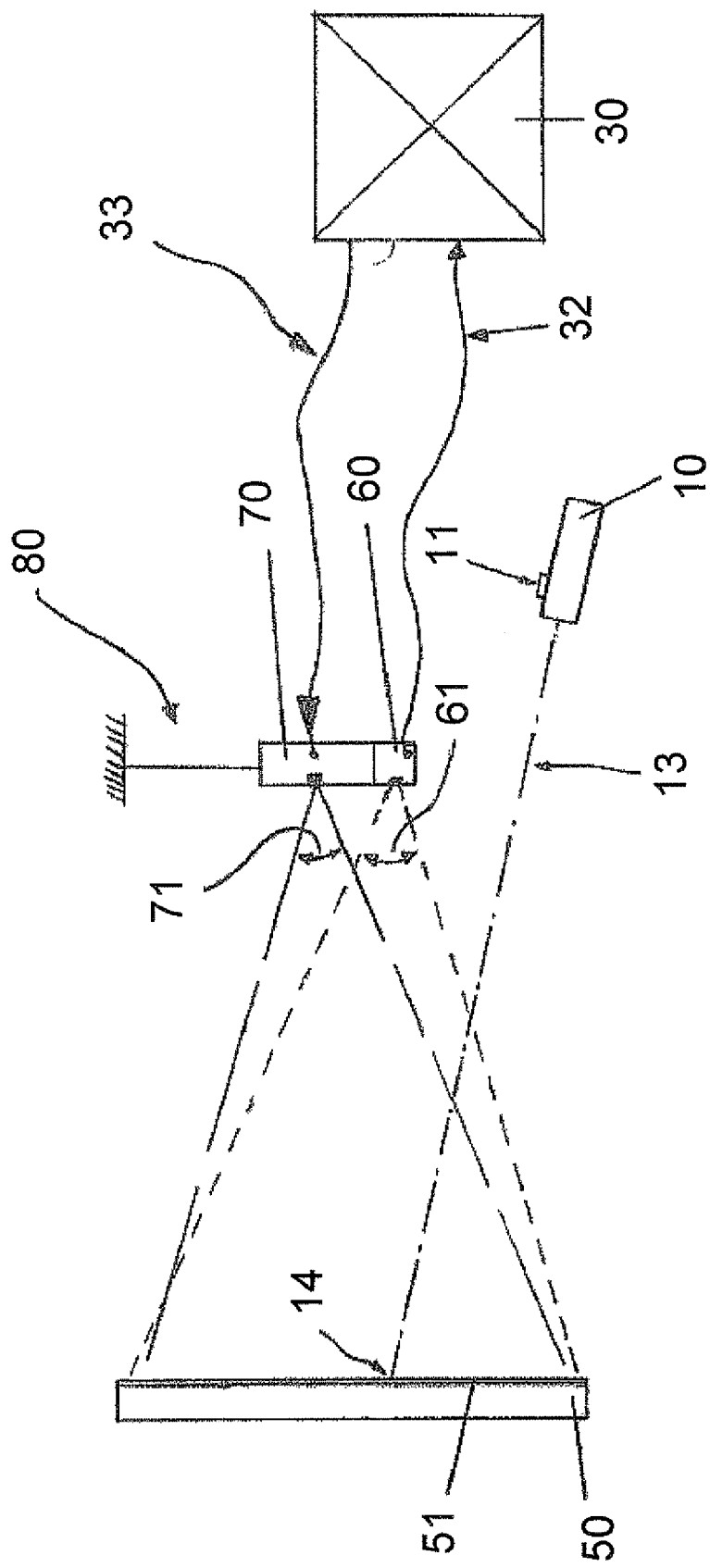
FIG. 4 depicts another embodiment of the present invention, using a projection system.

A somewhat different embodiment, which however also shows a system in accordance with the present invention, is depicted in FIG. 4. FIG. 4 again shows a laser pointer 10 with a button 11 for triggering a light beam 13. However, said light beam 13 is emitted in order to place a cursor on a projection screen 50, i.e. on the reflective surface 51 of said projection screen 50. Contrary to the foregoing examples, the projection screen 50 is a passive element which merely reflects radiation beamed upon it. It is shown in a side view, hence it is not possible to see what is being projected onto it but it is possible to see the arrangement of the other important elements of the system of FIG. 4, which include a projector 70 which is connected to a medical navigation system 30 and which can project images onto the display such as those shown on the display 20 in FIGS. 1 to 3. To this end, the projection field 71 of the projector 70 is configured to exactly cover the projection screen 50 in order to show as large a picture as possible. This large picture may be particularly expedient if the procedure being followed is to be communicated to an audience, for example during a demonstration or presentation.

In order to detect the image reflected by the screen 50 (or its reflective surface 51), a camera 60 exhibiting a field of view 61 is provided. The camera 60 is used as a light detection device and "sees" the navigation display on the screen 50, including the cursor 44. The camera can then on the one hand communicate this raw image to the navigation system 30 which can include a converter which converts the presence and location of the cursor 44 into navigationally usable information. On the other hand, such a converter can also be included in the camera 60, such that pre-processed information can be provided to the navigation system 30. Detecting the position is made easier if the camera 60 and projector 70 are arranged such that they have a predetermined positional relationship (i.e. in a calibrated system), for example a fixed positional relationship such as in FIG. 4, in which they are integrated into a single unit, although they can be composed of two separate parts attached to each other.

The medical navigation system 30, having received the information about the presence of the cursor 14 and its location relative to the projected image, can then process commands and control and/or operating inputs in the same manner as described above with respect to FIGS. 1 to 3 and can carry out the same or other actions which in turn influence the image projected by the projector 70, as indicated in FIG. 4 by the arrow 33 which represents a communication line between the navigation system 30 and the projector 70.

The projector 70 and the camera 30 can be arranged in accordance with the available space, but should be fixed once installed, as indicated by the fixation means 80.

A system as shown in the examples of FIGS. 1 to 4 enables the surgeon to work very time-effectively and to interact with the navigation system without any need to be close to the display. Laser pointers are very cheap and small and can therefore be integrated into almost any instrument. The surgeon can exactly locate the laser target point, hence control can be exercised with a high degree of reliability. Any other laser-equipped instruments in the operating room can also be used as a laser pointer or light pointer of the present invention, such that the present invention can be very easily integrated into an existing operating room set-up.

The invention claimed is:

1. A system for controlling or operating a medical device associated with a display on which medical images or control or operating elements are displayed, the system comprising:
a light pointer which projects a single delimited light cursor, wherein the light pointer comprises switchable or selectable light sources of one or more wavelengths, or a wavelength modifier, as its light source, or wherein the light pointer comprises a switchable or controllable cursor-forming unit for forming the projected light cursor, the light pointer further comprising a multi-deck switch for controlling light projection, the multi-deck switch exhibiting a first triggering point for producing the light cursor, and a second triggering point for changing the light properties of the light cursor;
a light detection device which is associated with the display and comprises a photosensitive surface or layer on the display for determining the presence and location and wavelength or form of the single light cursor projected by the light pointer; and
a converter which converts the captured presence and location information into control or operating commands for the medical device, wherein the converter is configured to create a variety of different control or operating commands or inputs assigned to different wavelengths or different forms of the light cursor.

2. The system according to claim 1, wherein the light pointer is a laser pointer.

3. The system according to claim 1, wherein the display is a monitor screen or a touch screen.

4. The system according to claim 1, wherein the light detection device comprises a position-detecting light grid or laser grid covering the surface of the display.

5. The system according to claim 1, wherein the light detection device comprises a camera or camera system which monitors the display.

6. The system according to claim 1, wherein the medical device is a medical or surgical navigation or treatment planning system.

7. The system according to claim 1, wherein the light pointer comprises a light slit or a lens or an object lens.

8. A method for controlling or operating a medical device associated with a display on which medical images or control or operating elements are displayed, the method comprising:
receiving a single delimited light cursor at a display, wherein the single delimited light cursor is projected onto the display by means of a light pointer, wherein the light pointer comprises switchable or selectable light sources of one or more wavelengths, or a wavelength modifier, as its light source, or wherein the light pointer comprises a switchable or controllable cursor-forming unit for forming the projected light cursor, and wherein the light pointer further comprises a multi-deck switch for controlling light projection, the multi-deck switch exhibiting a first triggering point for producing the light cursor, and a second triggering point for changing the light properties of the light cursor;
detecting the presence and location and wavelength or form on the display of the single light cursor projected by the light pointer by means of a photosensitive surface or layer on the display; and
converting the captured presence and location information into control or operating commands for controlling or operating the medical device, comprising creating a variety of different control or operating commands or inputs assigned to different wavelengths or different forms of the light cursor.

9. The method according to claim 8, wherein the medical device is controlled or operated in one or more of the following ways:
a control command or input is effected by pointing the light cursor at a spot for a predetermined or extended period of time;
a control command or input is effected by pointing the light cursor at a spot, projecting the cursor at a first wavelength in order to highlight an element on the display, and then changing the wavelength in order to effect a control or operating command with respect to the element;
a control command or input is effected by pointing the light cursor at a spot and then projecting a predetermined succession of light beams in order to effect a control or operating command with respect to the element;

a control command or input is effected by pointing the light cursor at a spot in order to highlight an element on the display and then projecting a predetermined succession of light beams in order to effect a control or operating command with respect to the element;
a control command or input is effected by pointing the light cursor at a spot on the display and then projecting a predetermined succession of light beams in order to effect a control or operating command with respect to the element;
a control command or input is effected by pointing the light cursor at a spot on the display in order to highlight an element on the display and then projecting a predetermined succession of light beams in order to effect a control or operating command with respect to the element;
a control command or input is effected by pointing the light cursor at a spot on the display and then altering the form of the cursor in order to effect a control or operating command with respect to the element;
a control command or input is effected by pointing the light cursor at a spot on the display in order to highlight an element on the display and then altering the form of the cursor in order to effect a control or operating command with respect to the element;
the cursor is made visible by highlighting an element on the display by means of a control software for the display.

\* \* \* \* \*